United States Patent [19]

Elist

[11] Patent Number: 5,669,870

[45] Date of Patent: Sep. 23, 1997

[54] PENILE IMPLANT FOR IMPROVED APPEARANCE

[76] Inventor: James J. Elist, 9301 Wilshire Blvd. #401, Beverly Hills, Calif. 90210

[21] Appl. No.: 662,707

[22] Filed: Jun. 13, 1996

[51] Int. Cl.⁶ ................... A61F 2/26; A61F 5/00
[52] U.S. Cl. ............................................. 600/40
[58] Field of Search ........................ 600/38–41

[56] References Cited

U.S. PATENT DOCUMENTS 4,628,912  12/1986  Fischell ..................... 600/40
4,773,403  9/1988  Daly ........................... 600/40

*Primary Examiner*—Lee S. Cohen
*Assistant Examiner*—Samuel Gilbert
*Attorney, Agent, or Firm*—Gene Scott-Patent Law & Venture Group

[57] ABSTRACT

An implant device improves the appearance of a penis that is misshapen, damaged or otherwise lacking in a natural anatomical appearance. A bellows like body being lengthwise expandable and generally flexible, is implanted between the penis shaft and the skin of the human penis. In the preferred embodiment, the body takes the shape of a double walled partial cylindrical sleeve, the walls having a bellows-like construction. A soft sponge material is positioned within the sleeve between the sleeve walls. When implanted, the body covers the shaft of the penis and extends in length between the glans penis and the base of the penis. One or more principally closed sacks is/are formed so that the device may receive a fluid from a fluid pressurization source. The present invention is well suited for patients that can achieve a natural erection, yet suffer from a penile malformity. The present device does not press inwardly on the shaft of the penis when pressurized, and further has a smooth, natural look and feel, both when the penis is flaccid as well as when it is erect.

9 Claims, 5 Drawing Sheets

PENILE IMPLANT FOR IMPROVED APPEARANCE

BACKGROUND OF THE INVENTION

1. Field of the Invention

This invention relates generally to penile implants and, more particularly, is directed towards an implant device for improving the appearance of a penis that is misshapen, damaged or otherwise lacks normal anatomical details.

2. Description of the Prior Art

Penile implants are known in the prior art. The following is a survey of the present state of he art:

Elist, U.S. Pat. No. 5,445,594 teaches an implant device for expanding the girth and length of a penis. A soft, flexible body is implanted between the shaft and the skin of the penis. The body takes the shape of a partial cylindrical sleeve that has an outer, relatively elastic sheet member and an inner, relatively inelastic sheet member. When implanted, the body covers the corpus cavernosum of the penis and does not or only partially covers the urethra, and extends in length between the glans penis and the base of the penis. A principally closed sack is formed between the inner and outer sheet members for receiving a fluid under pressure from a fluid source. Spring-like ribs are embedded within the inner sheet member for preventing collapse of the inner sheet member when the body is deflated.

Trick, U.S. Pat. No. 5,101,813 discloses a sterile, fully assembled, multi-component, penile erectile system which is to be surgically implanted in man for the treatment of erectile impotence. The system includes at least one elongated, flexible cylindrical member with a pressure chamber for implanting into the pendulous penis; a pressure bulb to be implanted in the scrotal sac; tubing integrally connecting the pressure chamber and the bulb to form a closed system; and, a system for adding or subtracting fluid from the system. The tubing is reinforced so that it will not collapse under suction or kink when bent. In one embodiment the pressure bulb is a multi-stroke pump and in another embodiment there is a receptacle for storing any tubing in excess of that required to extend between two or more components in a given patient. A method of sterilizing and packaging the system so that it can be provided to a surgeon assembled, filled and sterile is also described.

Zinner et al., U.S. Pat. No. 5,069,201 teaches a penile prosthesis which includes proximal and distal end portions with an intermediate normally flexible, nondistensible, collapsible main body portion that adjoins the proximal and distal portions. The main body portion includes filler elements that, in some embodiments of the invention, limit radial expansion of a rigidification chamber of the main body portion, and in other embodiments, limit radial constriction of the rigidification chamber. In some embodiments of the invention, rigidification is accomplished by movement of fluid into a rigidification chamber and in other embodiments of the invention rigidification is accomplished by movement of fluid out of a rigidification chamber. The prosthesis includes a manually manipulatable pumping arrangement to establish the necessary fluid movement for development of an erectile condition or a flaccid condition as desired.

Lue et al., U.S. Pat. No. 4,982,731 teaches a method and system for augmenting penile erection in a human male. An inflatable cuff is placed circumferentially around the corpora carvemosa, the deep dorsal vein, and the cavernous veins, adjacent to the hilum of the penis. Selective compression of the cuff will function to restrict venous drainage to augment penile erection. The cuff is adapted to have opposite ends thereof attached together and at least one inflatable vesicle is formed on the inner side of the cuff. A pump, including an attendant control system, is sized for implantation in a scrotum whereby the pump can be selectively squeezed to inflate and fluid pressurize the vesicle to compress the cuff around the penis. A control circuit, connected between the cuff and the pump, functions to automatically deflate the cuff after a predetermined period of time has elapsed.

Trick, U.S. Pat. No. 4,917,110 discloses an implantable prosthesis for correcting erectile impotence. The prosthesis includes at least one penile implant with a pressure chamber, an accumulator charged with fluid, tubing connected the accumulator to the pressure chamber of the implant, a valve which is normally closed, and a lever which can be moved to open the valve so that pressurizing fluid will flow from the accumulator into the pressure chamber.

Trick et al., U.S. Pat. No. 4,726,360 discloses a penile prosthesis which is adapted to be surgically implanted in man for the treatment of erectile impotence. The prosthesis includes at least one elongated, flexible cylindrical member which is adapted to be implanted into the corpus cavernosum of the pendulous penis, a pressure bulb for pressurizing liquid, and tubing connecting the member and the bulb. The member includes an inner non-distensible pressure chamber and an outer distensible chamber. The two chambers are connected by a passage and a valve for controlling flow through the passage so that fluid can be transferred from the pressure bulb, via the pressure chamber, to the outer chamber to cause it to distend, and in turn increase penile girth.

Whitehead, U.S. Pat. No. 4,665,903 teaches a prosthetic device for implantation within the penis which has a pumping mechanism that is integral with, and is in fluid communication with two fluid storage sections. Fluid is pumped manually from the proximal storage section to distal storage section and then to four distal expansile sections that inflate to render the penis rigid and capable of sexual activity. Undesirable shrinkage of the erect penis is avoided through a rigid frame and bellows that prevent the proximal reservoir from contracting longitudinally and radially as fluid is withdrawn from this storage section to produce the erect penis.

Yachia et al., U.S. Pat. No. 4,523,584 discloses a penile erectile system for treating male impotency. The system comprises a sleeve of biocompatible material having at least one pressurizable chamber which is adapted to be implanted about the penile shaft of a patient. A fluid reservoir of pressurizing fluid, and a pump for transferring the fluid under pressure from the reservoir to the chamber is placed beneath the penile skin, between the skin and the shaft. The system also includes tubing connecting the reservoir and pump to the pressurizable chamber, and a valve for controlling the flow of fluid into, and out of, the pressurizable chamber. In a preferred embodiment, a pressure bulb serves both as the fluid reservoir and the pump.

Schroeder, U.S. Pat. No. 4,407,275 discloses a semi-rigid annular ring having individual expandable chambers on the internal wall that are distended separately by fluid pressure. A multi-port flexible conduit is connected to the ring, having individual ports for each chamber. Fluid pressure is supplied through the conduit manually by a bulb, or electrically by a pump through a circular valve plate allowing the chambers to expand and contract in linear sequence. When a penis is placed into the ring and fluid pressure is applied, blood is forced to the end of the organ through the successive expansion and contraction of the bellows in wave fashion mechanically creating an erect condition of the organ.

Trick, U.S. Pat. No. 4,369,771 discloses a simple, reliable pressure control valve for a medical device having a hydraulic system. The system is comprised of a valve housing having an open top and a bottom and an inwardly directed shoulder partially closing the top; a poppet with an upwardly extending stem mounted in the housing between the top and the bottom; a sealing edge mounted on the poppet circumferentially about the stem, and a calibrated spring urging the poppet towards the open top of the housing so that the sealing edge is in sealing contact with the underside of the shoulder and the stem extends above the top of the housing so that manual pressure can be exerted upon the stem to open the valve, or the valve can be opened by a hydraulic pressure which exerts sufficient force upon the top of the poppet to overcome the force of the spring.

Rogers, U.S. Pat. No. 4,281,648 discloses an inflatable condom, prophylactic or prosthetic device having conventional anterior portion and retaining ring or reinforced edge with an expandable secondary portion extending from the anterior member, and having an air duct extending inside the anterior portion in communication with the secondary portion to facilitate controlled inflation of the secondary portion responsive to manipulation of a pressure bulb.

Yamanaka, U.S. Pat. No. 4,235,227 teaches an artificial corpus cavernosum device which is designed to be implanted into the imaired penis of a patient for the remedy of his impotence. The device comprises at least one artificial corpus cavernosum penis of elongated tubular pouch made of an artificial thin membrane to be implanted into the penis and for selectively receiving and being filled with a fluid for erecting the penis, a container made of an artificial thin membrane for storing the fluid under the normal condition when the penis is not inflated, and hence not erected, the container means being implantable into the scrotum, a slenderized conduit means for connecting at least one artificial corpus cavernosum penis to the container means in fluid communication with one another, and a check valve interposed in fluid communication with the container means, and having a valve member provided with a through-hole(s) for allowing the fluid, once forcibly delivered from the container means, to pass to the artificial corpus cavernosum penis and to return to the container means again little by little through the through-hole(s).

Finney, U.S. Pat. No. 4,204,530 discloses an implantable sleeve for increasing the penile diameter. The sleeve includes a flexible sheet of soft, physiologically acceptable implantable material, the sheet being of sufficient length when formed in the general shape of a cylindrical sleeve to extend from the glans penis to the base of the penis, and of a width which is insufficient to completely encircle the penis, but sufficient to cover the corpora cavernosa. The sheet preferably has edges which are rounded and tapered side edges. The sleeve also includes suturing strips on the inside wall of the sleeve, adjacent the side edges of the sheet, which facilitate the suturing of the sheet to the tunica albuginea. The sleeve further includes porous patches located on the interior of the inside wall of the sleeve into which fibroblasts from the underlying tissues can grow to further anchor the sleeve to the tunica albuginea. In the preferred embodiment, the sheet is of very soft, medical grade silicone elastomer, and suturing strips are of Dacron fabric and the porous patches are of Dacron fabric or fluff.

Clearly, then, there is a need for a penile implant device that is primarily directed at improving penile appearance, and can accommodate natural changes is penile length without causing discomfort. Such a needed device would not press inwardly on the shaft of the penis during especially during erection. Further, such a device would have a smooth, natural look and feel, both while the penis is flaccid as well as when it is erect. The present invention fulfills these needs and provides further related advantages.

SUMMARY OF THE INVENTION

The present invention is an implant device for improving the appearance of a penis that is misshapen, damaged or otherwise lacking in a natural anatomical appearance. A bellows like body being lengthwise expandable and generally flexible, is implanted between the penis shaft and the skin of the human penis. In the preferred embodiment, the body takes the shape of a double walled partial cylindrical sleeve, the walls having a bellows-like construction. A soft sponge material is positioned within the sleeve between the sleeve walls. When implanted, the body covers the shaft including the corpus cavernosum of the penis and extends in length between the glans penis and the base of the penis. One or more principally closed sacks is/are formed, so that the device may receive a fluid from a fluid pressurization source. The present invention is well suited for patients that can achieve a natural erection, yet suffer from a penile malformity. When pressurized, the implant expands radially to increase the girth of the penis but does not press inwardly on the corpus cavernosum, arteries and veins, or the urethra of the penis, and further has a smooth, natural look and feel, both when the penis is flaccid as well as when it is erect.

The fact that the implant provides an enhanced girth makes it ideal for use on patients with a less then average penile diameter, who wish to increase the diameter of the penis for vanity reasons, or who have surgical malformities. Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention a penile implant. In such drawings.

DETAILED DESCRIPTION OF THE PREFERRED EMBODIMENT

Figure 1:
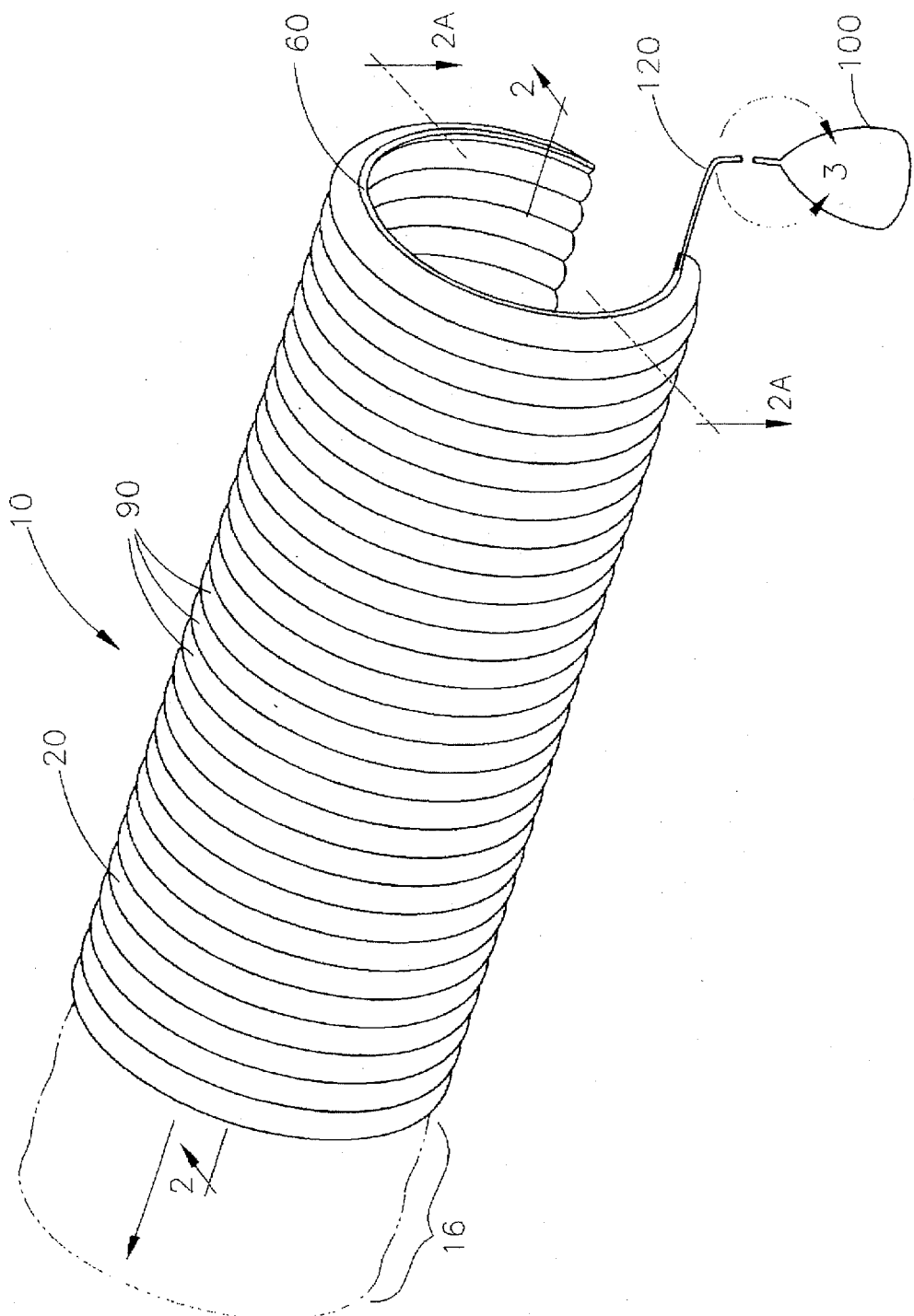
FIG. 1 is a perspective illustration of the present invention, a penile implant for improving the appearance of a human penis, illustrating a U-shaped outer partial cylindrical wall interconnected with a fluid storage means by a flexible tube, the partial cylindrical wall is constructed like a bellows which may expand and contract longitudinally, as shown at the left side of the figure.
Figure 2:
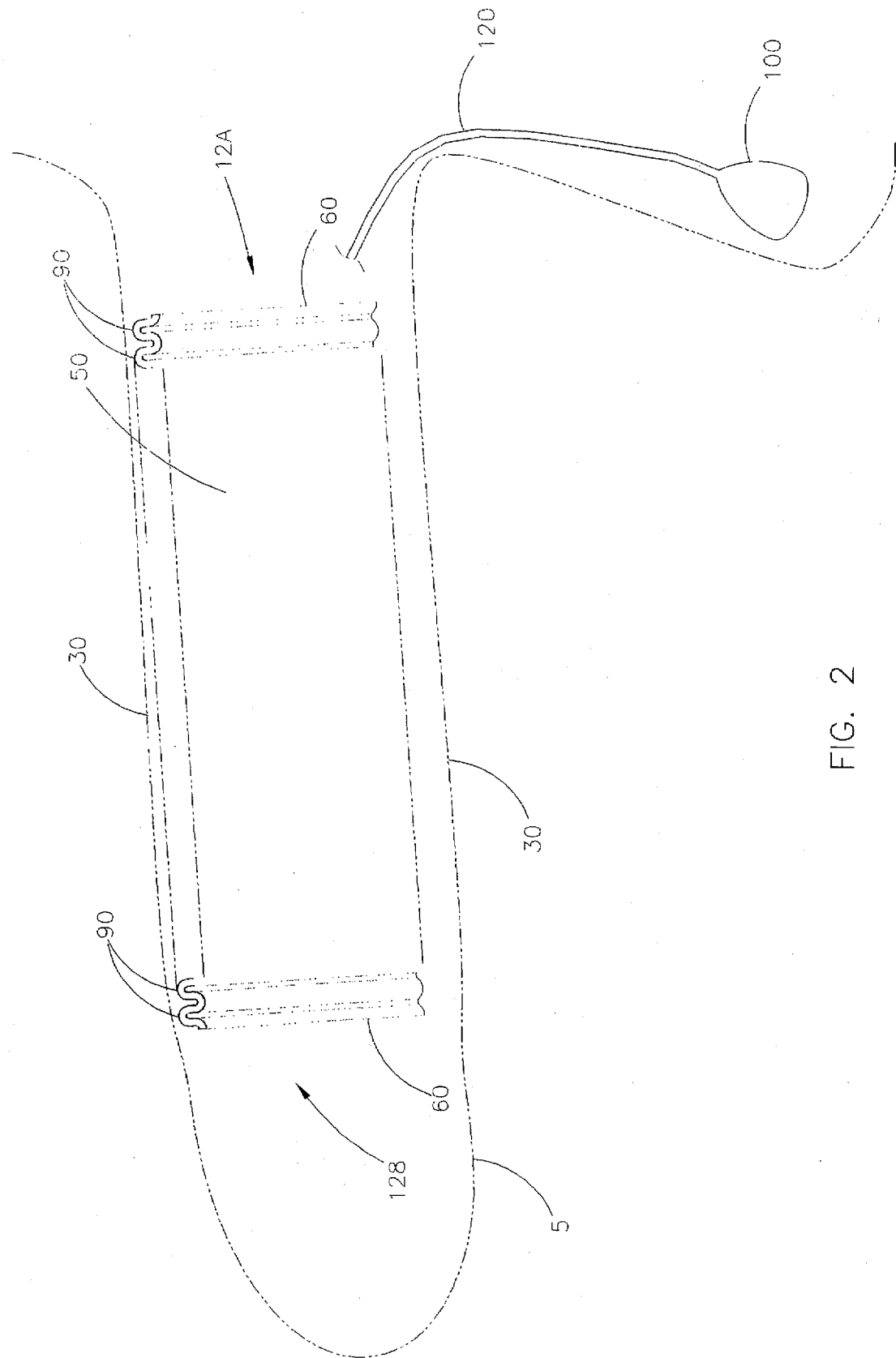
FIG. 2 is a cross-sectional view thereof, particularly of the partial cylindrical wall, and taken generally along line 2—2 of FIG. 1 and also showing the location of the implant within the penis and the preferred location of the fluid storage means within the testis.
Figure 2A:
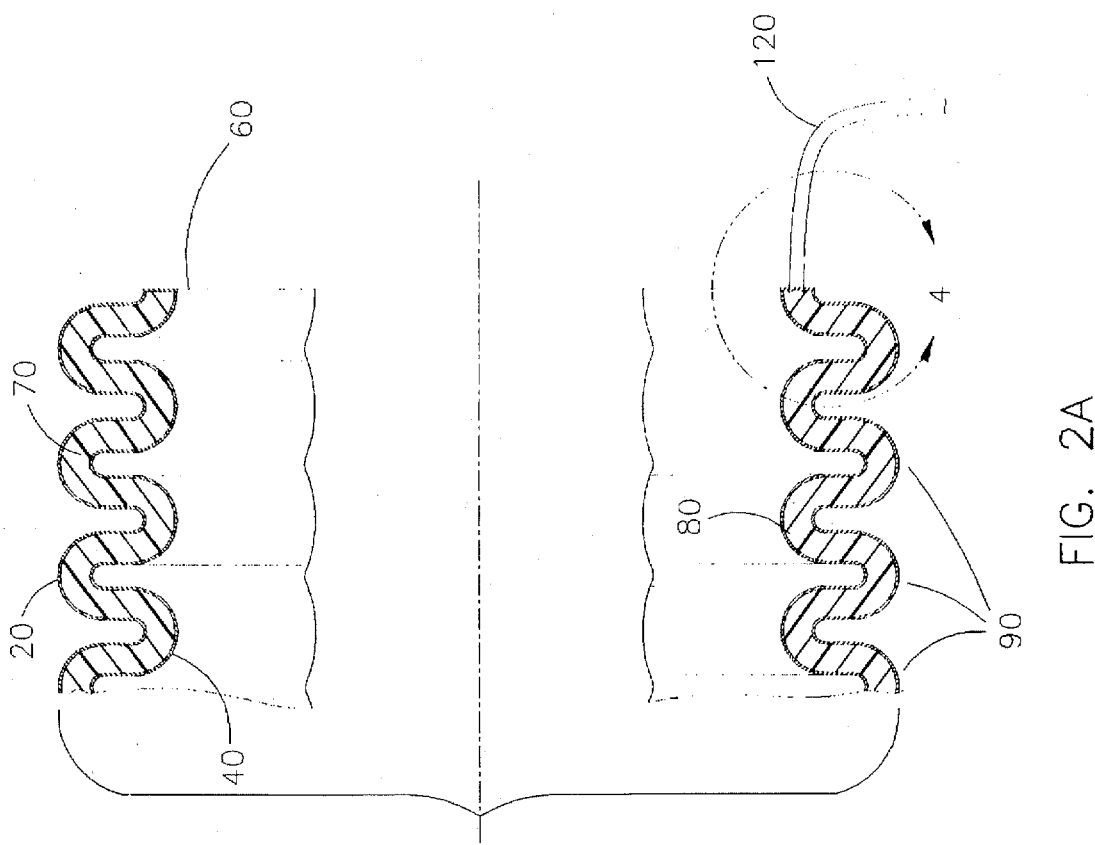
FIG. 2A is an enlarged partial cross-sectional view of the right end of the partial cylindrical wall as shown in FIG. 1 and taken along the line 2A—2A of FIG. 1.

The present invention, as shown in the figures, is a penile implant for providing a natural appearance to a malformed or small human penis 5. The implant provides a flexible double walled U-shaped partial cylindrical tube 10, and having, concentrically oriented, an outside partial cylindrical wall 20 positioned under a penile outer skin 30, and an inside partial cylindrical wall 40 positioned around a penile shaft 50, both of the ends 12A, 12B of the partial cylindrical tube 10 are closed between the outside 20 and the inside 40 walls by a membrane-like end wall 60. Positioned between the inside 20 and outside 40 partial cylindrical walls, and attached to the end walls 60 at both ends 12A, 12B of the partial cylindrical tube 10, is an elastic, absorbent, sponge material 70 engorged with a liquid 80, preferably a saline solution. The outside 20 and the inside 40 walls each provide a plurality of annular, circumferential folds 90 in the manner of a bellows, enabling longitudinal extension and retraction of the partial cylindrical tube 10 as well as general flexibility, with changes in penile length. FIG. 1 shows, in phantom line, a portion 16 of the partial cylindrical tube 10 as expanded lengthwise. The walls 20, 40 are preferably made of an impregnated fabric so that they are impermeable. The folds 90 provide circumferential rigidity to the partial cylindrical tube 10 so that it is not easily crushed, and the inside wall 40 is reinforced so that pressure within the partial tube 10 does not cause the inner wall 40 to press inwardly on the shaft 50 of the penis 5. However, the outer wall 20 tends to expand in diameter with increased pressure within the tube 10. The sponge material is preferably a material made by Merocel, Inc. of Mystic, Conn. It is a special sponge that expands by about 25% when it is wet.

Thus, upon engorgement, the sponge material tends to cause the partial cylindrical tube 10 to assume a larger diameter. Thus it has been found, determined, and invented that a U-shaped partial cylinder, constructed as a double walled bellows, provides, as an implant, a superior and unique structural capability to the human penis and provides appropriate support to the penis when flaccid as well as erect, so that a damaged or malformed penis provided with the implant of the present invention may function as well as any normal penis while assuming a normal anatomical configuration.

Figure 3B:
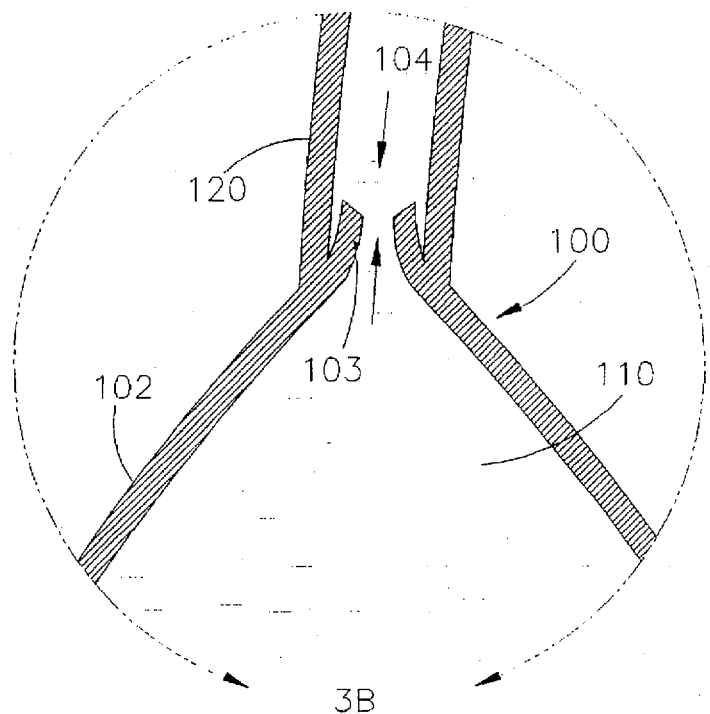
FIG. 3B is an enlarged partial view taken along line 3 in FIG. 1 and showing a portion of the fluid storage means showing a valve of the fluid storage means in an open state.
Figure 3A:
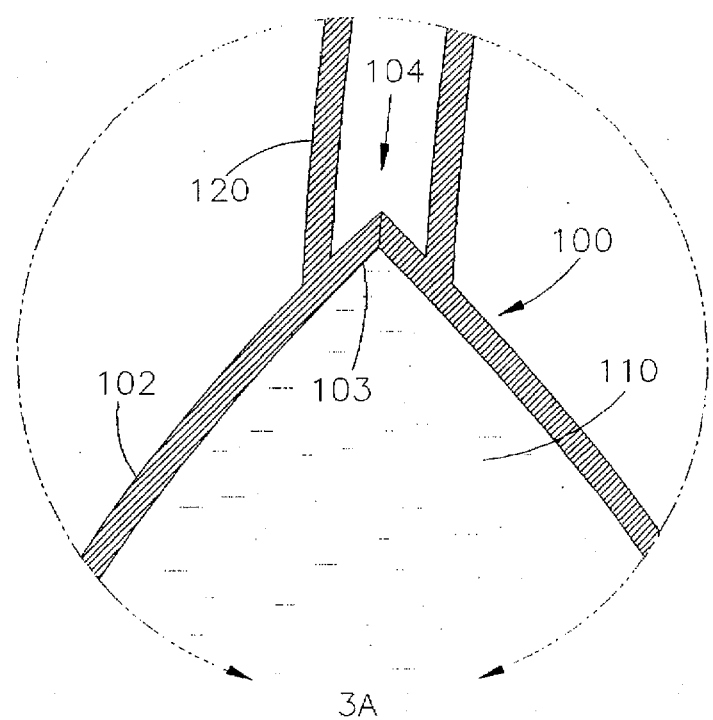
FIG. 3A is an enlarged partial view taken along line 3 in FIG. 1 and showing a portion of the fluid storage means showing a valve of the fluid storage means in a closed state.

The implant further includes, as best seen in FIGS. 1, 3A and 3B, a means for storing 100 a portion 110 of the liquid 80. The storing means 100 preferably a small bulb of flexible material such as silicon robber, is in liquid communication with the sponge material 70 by a flexible means for liquid conduction 120 such as a flexible tube, the storing means 100 providing a flexible wall 102 for pressurizing the liquid conduction means 120 and further providing a one-way valve 104 functionally allowing the portion 110 of the liquid 80 to flow from the storing means 100 to the conduction means 120 but not the reverse, i.e., from the conduction means 120 to the storing means 100. As shown in FIG. 3A and FIG. 3B, the one-way valve is preferably an annular lip 103 that is forced open when the storing means 100 is pressurized by pressing on wall 102. However, the lip tends to tightly close if the liquid 80 tries to flow back into the storing means 100.

Figure 4:
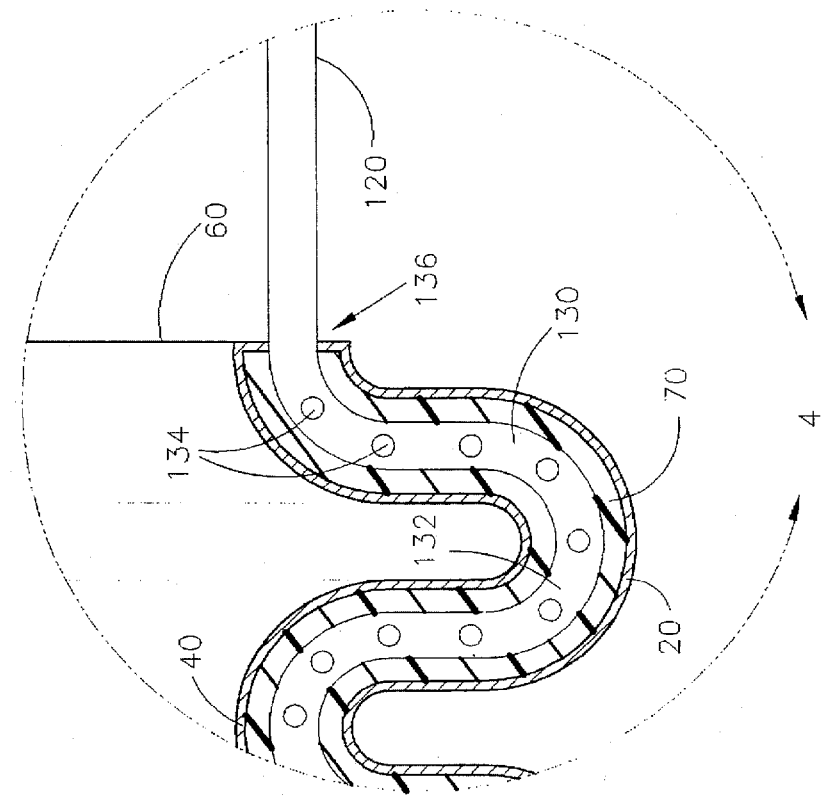
FIG. 4 is an enlarged partial view taken along line 4 in FIG. 2A.

The implant further includes, as best seen in FIG. 4, a distribution tube means 130 comprising an annular tube wall means 132, with a plurality of outlet hole means 134 positioned in it. The distribution tube means 130 is positioned within the partial cylindrical tube 10 preferably within the sponge material 70. One end 136 of the distribution tube means 130 is in liquid communication with the liquid conduction means 120 for conducting the liquid 80 into the partial cylindrical tube means 10. The distribution tube means 130 preferably extends from one end 12A to the other end 12B of the partial cylindrical tube 10 so that the liquid 80 may be delivered to the sponge material 70 uniformly.

Figure 5:
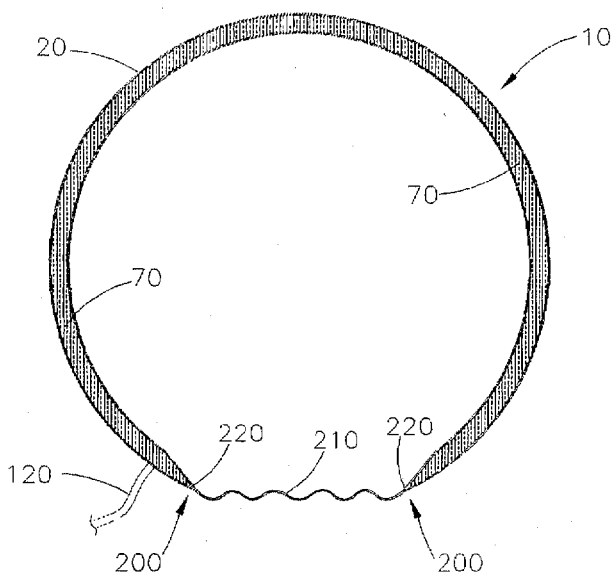
FIG. 5 is a schematic diagram showing an elevational view of a cross-section of an alternate embodiment of the invention.
Figures 6, 7:
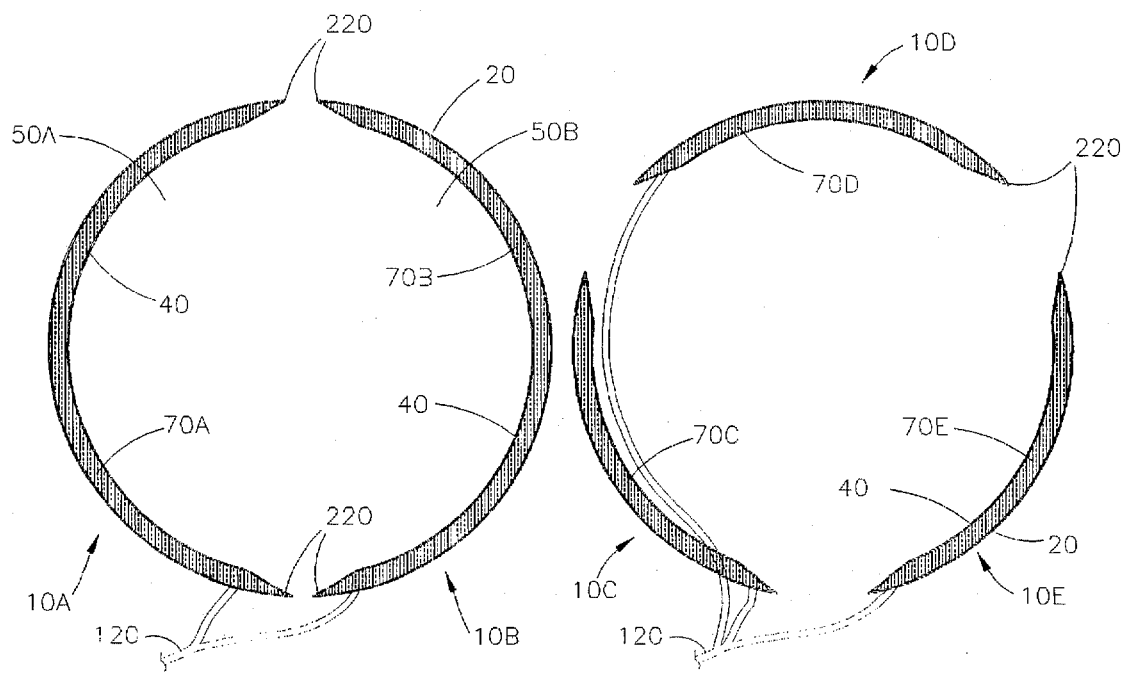
FIG. 6 is a schematic diagram showing an elevational view of a cross-section of a further alternate embodiment of the invention.
FIG. 7 is a schematic diagram showing an elevational view of a cross-section of a still further alternate embodiment of the invention.

As shown in FIG. 5 the partial cylindrical tube 10 may be one continuous and integral piece. In this case, the ends 200 of the tube 10 may be separated, or alternatively may be joined with a flexible sheet 210. Alternately, as shown in FIG. 6, the tube 10 may comprise two separate and separable portions 10A and 10B, each of the portions having the outside 20 and the inside 40 partial cylindrical walls joined along longitudinally directed seams 220 to form two closed chambers, filled with portions 70A and 70B respectively, of the sponge material 70. Preferably, the two portions 10A and 10B are positioned around opposing sides 50A and 50B respectively of the penile shaft 50. In a still further embodiment of the invention, as shown in FIG. 7, the tube 10 may comprise three separate and separable portions 10C, 10D and 10E, each of the portions having the outside 20 and the inside 40 partial cylindrical walls joined along longitudinally directed seams 220 to form three closed chambers filled with portions 70C, 70D and 70E respectively, of the sponge material 70. Preferably, the three portions 10C–E are positioned around the penile shaft 50 approximately as shown in FIG. 7.

In use, pressurizing of the cylinder 10, by pressing on the wall 102 of storage means 100 to drive the fluid 110 into the sponge material 70 causes the partial cylindrical tube 10 to assume a firm and normal penis like appearance both in the flaccid and the erect states of the penis. Since the sponge material 70 tends to expand when wet, the penis takes on a larger overall diameter. During changes in penile state, the partial cylindrical tube walls 20, 40 extend or retract as necessary to accommodate the required length of penis 5, and remain firm due primarily to the bellows structure, the sponge material 70, and the pressure level of the liquid 80 within the partial cylindrical tube 10.

While the invention has been described with reference to a preferred embodiment, it is to be clearly understood by those skilled in the art that the invention is not limited thereto. Rather, the scope of the invention is to be interpreted only in conjunction with the appended claims.

What is claimed is:

1. A penile implant for providing a natural appearance to a malformed penis, the implant comprising:

a flexible double walled partial cylindrical tube providing, concentrically oriented, an outside partial cylindrical wall adapted to be positioned under a penile outer skin, and an inside partial cylindrical wall adapted to be positioned around a penile shaft, both of the ends of the partial cylindrical tube being closed between the outside and the inside walls by a membrane-like end wall;

and positioned between the inside and outside partial cylindrical walls, and attached to the end walls at both ends of the partial cylindrical tube, an elastic, absorbent, sponge material impregnated with a liquid; the outside and the inside walls each providing a plurality of annular, circumferential folds enabling longitudinal extension and retraction of the partial cylindrical tube with changes in penile length.

2. The implant of claim 1 further including a means for storing a portion of the liquid, the storing means being in liquid communication with the sponge material by a flexible means for liquid conduction, the storing means providing a flexible wall for pressurizing the liquid conduction means and further providing a one way valve functionally allowing the liquid to flow from the storing means to the conduction means while preventing the liquid from flowing from the conduction means to the storing means.

3. The implant of claim 2 further including a distribution tube means comprising an annular tube wall means for conducting the liquid, the wall means having a plurality of outlet hole means therein for distributing the liquid, the distribution tube means positioned longitudinally within the partial cylindrical tube, one end of the distribution tube means in liquid communication with the liquid conduction means for conducting the liquid into the partial cylindrical tube.

4. The implant of claim 1 wherein the partial cylindrical tube comprises two separate and separable portions, each of the portions having the outside and inside partial cylindrical walls joined along longitudinally directed seams to form a closed chamber filled with a portion of the sponge material, the two portions being positioned laterally on opposing sides of the penile shaft.

5. The implant of claim 4 further including a means for storing a portion of the liquid, the storing means in liquid communication with the sponge material portions of the separable partial cylindrical tube portions by a flexible means for liquid conduction, the storing means providing a flexible wall for pressurizing the liquid conduction means and further providing a one way valve functional for allowing the liquid to flow from the storing means to the conduction means while preventing the fluid from flowing from the conduction means to the storing means.

6. The implant of claim 5 further including a means for distribution of the liquid within the partial cylindrical tube portions, the distribution means having a tube means comprising an annular tube wall means for conducting the liquid, the wall means having a plurality of outlet hole means therein for distributing the liquid, the distribution tube means positioned longitudinally within the partial cylindrical tube portions, of the distribution tube means in liquid communication with the liquid conduction means for conducting the liquid into the partial cylindrical tube portions.

7. The implant of claim 1 wherein the partial cylindrical tube comprises three separate and separable portions, each of the portions having the outside and inside partial cylindrical walls joined along longitudinally directed seams to form a closed chamber filled with a portion of the sponge material, the three portions being positioned around the penile shaft.

8. The implant of claim 7 further including a means for storing a portion of the liquid, the storing means in liquid communication with the sponge material portions of the separable partial cylindrical tube portions by a flexible means for liquid conduction, the storing means providing a flexible wall for pressurizing the liquid conduction means and further providing a one way valve functional for allowing the liquid to flow from the storing means to the conduction means and for preventing the fluid from flowing from the conduction means to the storing means.

9. The implant of claim 8 further including a means for distribution of the liquid within the partial cylindrical tube portions, the distribution means having a tube means comprising an annular tube wall means for conducting the liquid, the wall means having a plurality of outlet hole means therein for distributing the liquid, the distribution tube means positioned longitudinally within the partial cylindrical tube portions, of the distribution tube means in liquid communication with the liquid conduction means for conducting the liquid into the partial cylindrical tube portions.

* * * * *